US010336854B2

(12) United States Patent
Stache et al.

(10) Patent No.: US 10,336,854 B2
(45) Date of Patent: *Jul. 2, 2019

(54) ALKOXYSILANE-FUNCTIONALIZED AND ALLOPHANATE-FUNCTIONALIZED URETHANES

(71) Applicant: Evonik Degussa GmbH, Essen (DE)

(72) Inventors: Wiebke Stache, Herten (DE); Tobias Unkelhäußer, Dülmen (DE); Annegret Lilienthal, Dorsten (DE); Tina Bauer, Gelsenkirchen (DE)

(73) Assignee: Evonik Degussa GmbH, Essen (DE)

( * ) Notice: Subject to any disclaimer, the term of this patent is extended or adjusted under 35 U.S.C. 154(b) by 185 days.

This patent is subject to a terminal disclaimer.

(21) Appl. No.: 15/619,897

(22) Filed: Jun. 12, 2017

(65) Prior Publication Data
US 2017/0369627 A1    Dec. 28, 2017

(30) Foreign Application Priority Data
Jun. 27, 2016    (EP) ..................................... 16176311

(51) Int. Cl.
| | |
|---|---|
| C08G 18/70 | (2006.01) |
| C08G 18/38 | (2006.01) |
| C08G 18/50 | (2006.01) |
| C08G 18/78 | (2006.01) |
| C08G 18/28 | (2006.01) |
| C08G 18/64 | (2006.01) |
| C08G 18/10 | (2006.01) |
| C08G 18/24 | (2006.01) |
| C08G 18/32 | (2006.01) |
| C08G 18/75 | (2006.01) |
| C09D 175/04 | (2006.01) |
| C09J 175/04 | (2006.01) |
| C08G 18/71 | (2006.01) |
| C08G 18/80 | (2006.01) |
| C08G 18/22 | (2006.01) |
| C07F 7/10 | (2006.01) |

(52) U.S. Cl.
CPC ............ *C08G 18/3893* (2013.01); *C07F 7/10* (2013.01); *C08G 18/10* (2013.01); *C08G 18/222* (2013.01); *C08G 18/242* (2013.01); *C08G 18/246* (2013.01); *C08G 18/289* (2013.01); *C08G 18/3206* (2013.01); *C08G 18/3831* (2013.01); *C08G 18/5096* (2013.01); *C08G 18/6469* (2013.01); *C08G 18/718* (2013.01); *C08G 18/755* (2013.01); *C08G 18/7837* (2013.01); *C08G 18/807* (2013.01); *C08G 18/809* (2013.01); *C09D 175/04* (2013.01); *C09J 175/04* (2013.01); *C09J 2475/00* (2013.01)

(58) Field of Classification Search
CPC ............ C08G 18/7837; C08G 18/6469; C08G 18/5096; C08G 18/289; C08G 18/3893; C08G 18/807; C08G 18/809; C08G 18/755; C09D 175/04; C09J 175/04
See application file for complete search history.

(56) References Cited

U.S. PATENT DOCUMENTS

| | | | | |
|---|---|---|---|---|
| 7,812,087 | B2 * | 10/2010 | Ludewig | ................ C08G 18/10 524/589 |
| 8,067,522 | B2 | 11/2011 | Ludewig et al. | |
| 8,163,390 | B2 | 4/2012 | Gruber et al. | |
| 9,175,126 | B2 | 11/2015 | Albrecht et al. | |
| 9,266,825 | B2 | 2/2016 | Lomoelder et al. | |
| 2010/0010113 | A1 | 1/2010 | Schwalm et al. | |
| 2015/0191625 | A1 | 7/2015 | Lomoelder et al. | |
| 2015/0232609 | A1 | 8/2015 | Spyrou et al. | |
| 2015/0329751 | A1 | 11/2015 | Stache et al. | |
| 2015/0329752 | A1 | 11/2015 | Albrecht et al. | |
| 2016/0297974 | A1 | 10/2016 | Stache et al. | |

FOREIGN PATENT DOCUMENTS

| | | |
|---|---|---|
| DE | 102005041953 A1 | 3/2007 |
| DE | 102005041954 A1 | 3/2007 |
| WO | 2008043722 A1 | 4/2008 |
| WO | 2013189882 A2 | 12/2013 |

OTHER PUBLICATIONS

Stache et al., U.S. Appl. No. 15/614,763, filed Jun. 6, 2017.
Stache et al., U.S. Appl. No. 15/622,159, filed Jun. 14, 2017.
Stache et al., U.S. Appl. No. 15/622,204, filed Jun. 14, 2017.

* cited by examiner

*Primary Examiner* — Michael L Leonard
(74) *Attorney, Agent, or Firm* — Philip P. McCann; Nexsen Pruet, PLLC

(57) ABSTRACT

The present invention relates to alkoxysilane-functionalized and allophanate-functionalized urethanes, methods for the preparation thereof, coating compositions comprising these and to the use thereof.

21 Claims, No Drawings

ALKOXYSILANE-FUNCTIONALIZED AND ALLOPHANATE-FUNCTIONALIZED URETHANES

This application claims the benefit of European Application No. 16176311.5 filed on Jun. 27, 2016, the disclosure of which is expressly incorporated herein by reference.

BACKGROUND

The present invention relates to alkoxysilane-functionalized and allophanate-functionalized urethanes, methods for the preparation thereof, coating compositions comprising these and to the use thereof.

Polyurethanes have been established for many decades as high-value components for paint, adhesive, sealant and plastics systems. It is possible here for additional alkoxysilane groups to play an important role, for example with regard to network density, chemical resistance and scratch resistance, primarily through the formation of siloxane and polysiloxane structures.

Molecules not only having alkoxysilane groups but also comprising isocyanate groups offer the option of introducing the functionalities that result as reaction products, siloxanes and polyurethane groups, through one component. Such substances have long been in use, for example in the form of isocyanatoalkyltrialkoxysilanes.

Alkoxysilane-terminated polyurethanes prepared from isocyanatoalkyltrialkoxysilanes and alcohols are also known and are used, for example, for producing highly crosslinked, rigid coating compositions (e.g. WO 2013/189882 A2). However, if these alkoxysilane-terminated polyurethanes are used as sole binder in systems that cure at room temperature, coatings are obtained with only moderate hardness.

Allophanate-containing binders have long been known. Alkoxysilane-functionalized allophanates are also known. There are several types that can be distinguished here, which are shown below, but correspond neither in terms of structure nor in the application to the alkoxysilane-functionalized allophanates according to the invention.

For instance, the allophanates III (1) described in WO 2008/043722 A1 are obtained by reacting NCO-terminated allophanate-containing polyurethanes I (1) with alkoxysilanes II (1) reactive to isocyanate (e.g. aminoalkyltrialkoxysilane). The allophanate groups here are therefore in the centre of the polyurethane chain and the alkoxysilane function is attached via the terminal isocyanate group in the context of a urea function (structure III (1), equation 1).

(Equation 1)

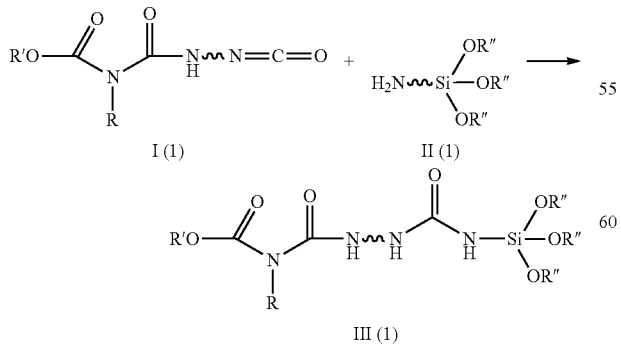

DE102005041953 A1 describes the reaction of a polyol I (2) having a mean molecular weight of 3000-20 000 g/mol with an excess of isocyanatopropyltrimethoxysilane II (2) so as to result, after polyurethane formation III (2), in the formation of an allophanate IV (2) having two alkoxysilane functions per allophanate unit.

(Equation 2)

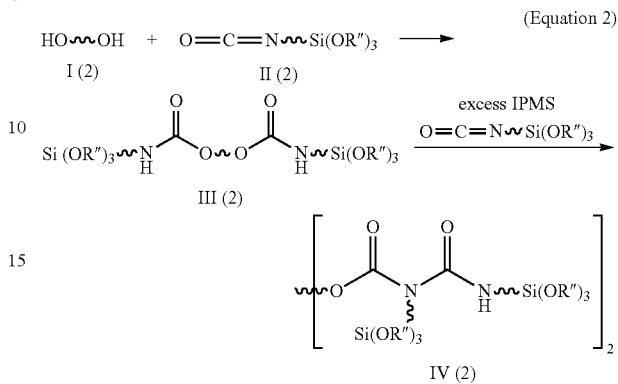

In DE102005041954 A1, a polyurethane I (3) is admixed with isocyanatopropyltrimethoxysilane II (3) and the mixture is heated until allophanate structures are formed. In this case, the alkoxysilane group is attached to the terminal nitrogen of the allophanate group (III) (3) (equation 3).

(Equation 3)

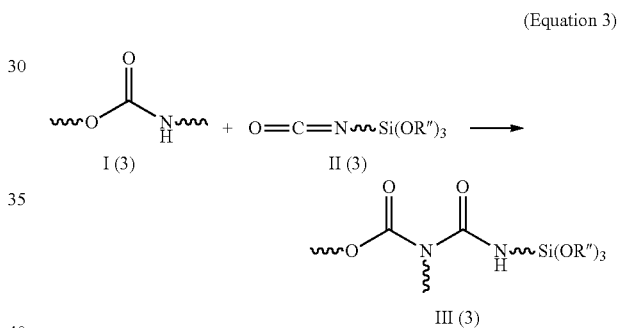

J. Kozakiewicz et al. published, in *Progress in Organic Coatings* 72 (2011) 120-130, the reaction of isocyanatopropyltrimethoxysilane I (4) with methanol to form the corresponding urethane II (4) and subsequently with hexamethylene diisocyanate trimer III (4). In the highly viscous allophanate IV (4) resulting therefrom, the alkoxysilane function is appended on the tertiary central amine of the allophanate group (equation 4).

(Equation 4)

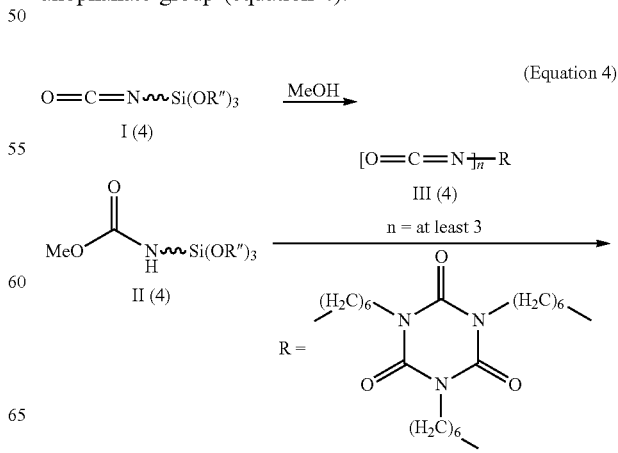

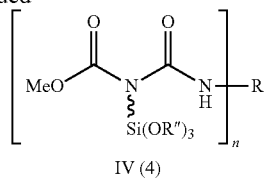

IV (4)

In the use described, the allophanate function serves as blocking agent for the hexamethylene diisocyanate trimer which was used as crosslinker for hydroxy-functionalized polyester polyols.

Even now, there exists a need for novel, silane-containing binders which have specific properties.

SUMMARY

The object of this invention was to make accessible novel silane-containing binders which are suitable for the development of highly crosslinked, rigid coatings.

This object is achieved by alkoxysilane-functionalized and allophanate-functionalized urethanes in accordance with the present invention.

Surprisingly, it has been found that the alkoxysilane-functionalized and allophanate-functionalized urethanes according to the invention are suitable for application as paint, adhesive or sealant. The alkoxysilane-functionalized and allophanate-functionalized urethanes according to the invention may be used particularly for the development of highly crosslinked, particularly rigid coatings. In this case, the alkoxysilane-functionalized and allophanate-functionalized urethanes according to the invention may be used as sole binder in both cold and hot curing.

DETAILED DESCRIPTION

The invention relates to alkoxysilane-functionalized and allophanate-functionalized urethanes comprising the reaction product of I.
A) at least one, preferably one, alkoxysilane group-containing monourethane A) of the formula 1

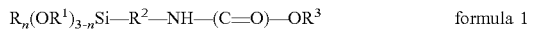

where $R_n$, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B),
in a molar ratio of A) to B) of from 1.0:1.5 to 1.0:0.6, preferably 1.15:1 to 0.85:1,
particularly preferably 1:1,
optionally in the presence of at least one catalyst K), II.
and the subsequent reaction
C) with at least one diol and/or polyol C),
optionally in the presence of at least one catalyst K),
in the ratio of the NCO groups of reaction product I. to the OH groups of the diol and/or polyol II. C) of from 1.0:1.5 to 1.0:0.6, preferably 1.15:1 to 0.85:1, particularly preferably 1:1.

In this case, alkoxysilane-functionalized and allophanate-functionalized urethanes, which comprise the reaction product mentioned, are particularly understood to mean urethanes which themselves consist of the reaction product of monourethane-diisocyanate adduct and diol/polyol or based on possible unreacted residues in the reaction product have been derivatized or further reacted. The reaction product mentioned is preferably a urethane, which itself consists of the reaction product of an adduct of monourethane and diisocyanate with a diol/polyol or based on possible unreacted isocyanate groups in the reaction product has been derivatized, i.e. reacted or capped. The reaction product mentioned is particularly preferably a urethane, which itself consists of an adduct of monourethane and diisocyanate in the molar ratio of 1.0:1.5 to 1.0:0.6, preferably 1.15:1 to 0.85:1, and a diol/polyol. The reaction product mentioned is especially preferably a urethane, which itself consists of a 1:1 adduct of monourethane and diisocyanate and a diol/polyol.

The adducts formed in step I, which can be seen from the reaction of at least one monourethane with at least one diisocyanate in the molar ratio of 1.0:1.5 to 1.0:0.6, preferably 1.15:1 to 0.85:1, are adducts having on average 0.6-1.5 allophanate units, since the diisocyanate can partially or completely react with one or two monourethanes. However, the adduct according to the invention preferably has on average one, preferably one, allophanate unit.

Subsequently, the adduct is reacted with at least one diol and/or polyol to react with hitherto unreacted isocyanate groups. A 1:1 adduct of monourethane and diisocyanate, which therefore still has one free isocyanate group, is preferably reacted with the at least one diol/polyol.

The alkoxysilane-functionalized and allophanate-functionalized urethane according to the invention is particularly preferably an adduct of one monourethane and one diisocyanate, which has subsequently been reacted with one diol/polyol to give an adduct with one allophanate and one urethane unit.

"One" monourethane, "one" diisocyanate, "one diol" or "one" polyol is understood to mean here in particular in each case the respective monourethane, diisocyanate, diol or polyol of an empirical formula.

The invention preferably provides alkoxysilane-functionalized and allophanate-functionalized urethanes consisting of the reaction product of I. and II. as defined above.

The invention also relates to alkoxysilane-functionalized and allophanate-functionalized urethanes, obtained by reacting I.
A) at least one, preferably one, alkoxysilane group-containing monourethane A) of the formula 1

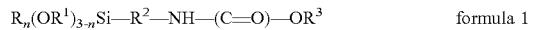

where $R_n$, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B),
in a molar ratio of A) to B) of from 1.0:1.5 to 1.0:0.6, preferably 1.15:1 to 0.85:1,
particularly preferably 1:1,
optionally in the presence of at least one catalyst K), II.
and the subsequent reaction
C) with at least one diol and/or polyol C),
optionally in the presence of at least one catalyst K),
in the ratio of the NCO groups of reaction product I. to the OH groups of the diol and/or polyol II. C) of from 1.0:1.5 to 1.0:0.6, preferably 1.15:1 to 0.85:1, particularly preferably 1:1.

Preferably $R_n$, $R^1$, $R^2$ and $R^3$ are at the same time or each independently methyl, ethyl, n-propyl, isopropyl, n-butyl, sec-butyl or tert-butyl.

Preferably, n=0.

$R^1$ and $R^3$ are preferably at the same time or each independently methyl or ethyl.

$R^2$ is preferably methyl or propyl.

Preferred compounds are those where n is 0, $R^1$ and $R^3$ are at the same time or each independently methyl or ethyl, and $R^2$ is at the same time or each independently methyl or propyl.

Preferably, $R^3=R^1$.

Preference is given to compounds where n is 0 and $R^2$ is methyl or propyl, and $R^1$ is methyl or ethyl and $R^3=R^1$.

Very particular preference is given to the compound where n is 0, $R^1$ and $R^3$ are methyl and $R^2$ is propyl, N-trimethoxysilylpropyl methylcarbamate.

The diisocyanate B) used in accordance with the invention may be any aliphatic, cycloaliphatic and/or (cyclo)aliphatic diisocyanate. In one preferred embodiment the term "(cyclo)aliphatic diisocyanate" as used herein means that in a molecule there are present simultaneously NCO groups bonded to a ring and NCO groups bonded to an aliphatic radical, as is the case, for example, for isophorone diisocyanate. In one preferred embodiment the term "cycloaliphatic diisocyanate" as used herein refers to a diisocyanate which only has NCO groups bonded directly on the cycloaliphatic ring, an example being diisocyanatodicyclohexylmethane (H12MDI).

Aliphatic diisocyanates preferably suitable for use as diisocyanate B) include linear and/or branched alkylene radicals having preferably 3 to 16 carbon atoms, more preferably 4 to 12 carbon atoms. Preferably suitable cycloaliphatic or (cyclo)aliphatic diisocyanates include a cycloalkylene radical having preferably 4 to 18 carbon atoms, more preferably 6 to 15 carbon atoms. Preferred examples of suitable diisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, such as 4-isocyanatomethyl-1,8-octane diisocyanate (TIN), decane di- and triisocyanate, undecane di- and triisocyanate, dodecane di- and triisocyanates. Likewise preferably suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

Preferred diisocyanates B) are isophorone diisocyanate hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-di cyclohexylmethane diisocyanate (4,4'-H12MDI), 2-methylpentane diisocyanate (MPDI), 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), individually or in mixtures.

In a particularly preferred embodiment, the diisocyanate B) is IPDI and/or 4,4'-H12MDI and/or HDI and/or a mixture of 2,2,4-TMDI and 2,4,4-TMDI.

Diols C) and polyols C) used are, for example, ethylene glycol, propane-1,2-diol, propane-1,3-diol, diethylene glycol, dipropylene glycol, triethylene glycol, tetraethylene glycol, butane-1,2-diol, butane-1,4-diol, butylethylpropane-1,3-diol, methylpropane-1,3-diol, pentane-1,5-diol, bis(1,4-hydroxymethyl)cyclohexane (cyclohexanedimethanol), glycerol, hexanediol, neopentyl glycol, trimethylolethane, trimethylolpropane, pentaerythritol, bisphenol A, bisphenol B, bisphenol C, bisphenol F, norbornylene glycol, 1,4-benzyldimethanol, 1,4-benzyldiethanol, 2,4-dimethyl-2-ethylhexane-1,3-diol, 1,4-butylene glycol, 2,3-butylene glycol, di-β-hydroxyethylbutanediol, pentane-1,5-diol, hexane-1,6-diol, octane-1,8-diol, decanediol, dodecanediol, neopentyl glycol, cyclohexanediol, 3(4),8(9)-bis(hydroxymethyl)tricyclo[5.2.1.0$^{2,6}$]decane (dicidol), 2,2-bis(4-hydroxycyclohexyl)propane, 2,2-bis[4-(β-hydroxyethoxy)phenyl]propane, 2-methylpropane-1,3-diol, 2-methylpentane-1,5-diol, 2,2,4(2,4,4)-trimethylhexane-1,6-diol, hexane-1,2,6-triol, butane-1,2,4-triol, 2,2-dimethylpropane-1,3-diol, heptane-1,7-diol, octadecen-9,10-diol-(1,12), thiodiglycol, octadecane-1,18-diol, 2,4-dimethyl-2-propylheptane-1,3-diol,tris(β-hydroxyethyl) isocyanurate, mannitol, sorbitol, polypropylene glycols, polybutylene glycols, xylylene glycol or neopentyl glycol hydroxypivalate, alone or in mixtures.

Particularly preferred diols C) and polyols C) are ethylene glycol, triethylene glycol, butane-1,4-diol, propane-1,2-diol, pentane-1,5-diol, hexane-1,6-diol, cyclohexanedimethanol, decanediol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol 3-methylpentane-1,5-diol, 2-methylpentane-1,5-diol, trimethylolpropane, 2,2-dimethylpropane-1,3-diol(neopentyl glycol), neopentylglycol hydroxypivalate and cis/trans-cyclohexane-1,4-diol, alone or in mixtures.

Especially preferred diols C) and polyols C) are pentane-1,5-diol, hexane-1,6-diol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) and cis/trans-cyclohexane-1,4-diol, alone or in mixtures.

As component C), preference is given to using hydroxyl group-containing polyesters, polyethers, polyacrylates, polycarbonates and polyurethanes having an OH number of 20 to 500 mg KOH/g and a mean molar mass of 250 to 6000 g/mol. Particular preference in the context of the present invention is given to using hydroxyl group-containing polyesters or polyacrylates having an OH number of 50 to 250 mg KOH/g and a mean molecular weight of 500 to 6000 g/mol. The hydroxyl number (OH number, OHN) is determined in accordance with DIN 53240-2. In the case of that method, the sample is reacted with acetic anhydride in the presence of 4-dimethylaminopyridine as catalyst, with the hydroxyl groups being acetylated. For each hydroxyl group, this produces one molecule of acetic acid, while the subsequent hydrolysis of the excess acetic anhydride yields two molecules of acetic acid. The consumption of acetic acid is determined by titrimetry from the difference between the main value and a blank value, which is to be carried out in parallel. The molecular weight is determined by means of gel permeation chromatography (GPC). The samples are characterized in tetrahydrofuran as eluent in accordance with DIN 55672-1.

As component C), it is possible to use hydroxyl group-containing (meth)acrylic copolymers which may be resins having a monomer composition of the kind described, for example, in WO 93/15849 (page 8, line 25 to page 10, line 5). In that case the acid number of the (meth)acrylic copolymer, to be set through proportional use of (meth)acrylic acid as monomer, ought to be 0 to 30, preferably 0 to 15 mg KOH/g. The number-average molar weight (determined by gel permeation chromatography against a polystyrene standard) of the (meth)acrylic copolymer is preferably 2000 to 20 000 g/mol; the glass transition temperature is preferably −40° C. to +60° C. and the hydroxyl content of the (meth)acrylic copolymers for use in accordance with the invention, to be set through proportional use of hydroxyalkyl (meth)acrylates, is preferably 20 to 500 mg KOH/g, particularly preferably 50 to 250 mg KOH/g.

Polyester polyols suitable as component C) in accordance with the invention are resins having a monomer composition composed of dicarboxylic and polycarboxylic acids and of diols and polyols, as described in WO 93/15849. Also employable as polyester polyols are polyaddition products of caprolactone onto low molecular weight di- and triols as are available under the trade name CAPA® (Perstorp) for example. The arithmetically determined number-average molar weight is preferably 500 to 5000 g/mol, particularly preferably 800 to 3000 g/mol; the average functionality is preferably 2.0 to 4.0, preferably 2.0 to 3.5.

Urethane- and ester-group-containing polyols which may in principle be used in accordance with the invention as component C) also include those which are described in EP 140 186. Preference is given to using urethane- and ester-group-containing polyols which are prepared using HDI, IPDI, trimethylhexamethylene diisocyanate (TMDI) or dicyclohexylmethane diisocyanate (H12MDI). The number-average molar weight is preferably 500-5000 g/mol; the average functionality lies more particularly in the range of 2.0-3.5.

Suitable as component C) are diols and polyols containing further functional groups. The familiar linear or branched hydroxy group-containing polyesters, polycarbonates, polycaprolactones, polyethers, polythioethers, polyesteramides, polyurethanes or polyacetals are concerned here. Their number-average molecular weight is preferably in the range from 134 to 3500 g/mol. Preference is given to linear hydroxyl group-containing polyesters—polyester polyols—or mixtures thereof. They are prepared, for example, by reaction of diols with sub stoichiometric amounts of dicarboxylic acids, corresponding dicarboxylic anhydrides, corresponding dicarboxylic esters of lower alcohols, lactones or hydroxycarboxylic acids.

Diols suitable for preparation of the polyester polyols are, as well as the abovementioned diols, also 2-methylpropanediol, 2,2-dimethylpropanediol, diethylene glycol, dodecane-1,12-diol, cyclohexane-1,4-dimethanol and cyclohexane-1,2- and -1,4-diol.

Dicarboxylic acids or derivatives suitable for preparation of the polyester polyols may be aliphatic, cycloaliphatic, aromatic and/or heteroaromatic in nature and may optionally be substituted, for example by halogen atoms, and/or unsaturated.

The preferred dicarboxylic acids or derivatives include succinic acid, adipic acid, suberic acid, azelaic acid, sebacic acid, 2,2,4(2,4,4)-trimethyladipic acid, phthalic acid, phthalic anhydride, isophthalic acid, terephthalic acid, dimethyl terephthalate, tetrahydrophthalic acid, maleic acid, maleic anhydride and dimeric fatty acids.

Suitable polyester polyols further include those which may be prepared in a known manner, via ring opening, from lactones such as epsilon-caprolactone, and simple diols as starter molecules.

The diols and dicarboxylic acids/derivatives thereof used for preparation of the polyester polyols can be used in any desired mixtures.

It will be appreciated that it is also possible to employ mixtures of the components C) described above.

The ratio of the NCO groups of reaction product I. to the OH groups of the diol and/or polyol II. C) varies from 1.0:1.5 to 1.0:0.6, preferably 1.15:1 to 0.85:1, particularly preferably 1:1.

The invention also relates to a method for preparing alkoxysilane-functionalized and allophanate-functionalized urethanes by reacting I.
A) at least one, preferably one, alkoxysilane group-containing monourethane A) of the formula 1

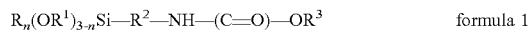

$R_n(OR^1)_{3-n}Si-R^2-NH-(C=O)-OR^3$     formula 1 where $R_n$, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B),
in a molar ratio of A) to B) of from 1.0:1.5 to 1.0:0.6, preferably 1.15:1 to 0.85:1,
particularly preferably 1:1
optionally in the presence of at least one catalyst K), II.
and the subsequent reaction
C) with at least one diol and/or polyol C),
optionally in the presence of at least one catalyst K),
in the ratio of the NCO groups of reaction product I. to the OH groups of the diol and/or polyol II. C) of from 1.0:1.5 to 1.0:0.6, preferably 1.15:1 to 0.85:1, particularly preferably 1:1.

The alkoxysilane-functionalized and allophanate-functionalized urethanes according to the invention are prepared in two steps. In step I. the monourethane A) is reacted with the diisocyanate B), which results in the reaction product I. Subsequently step II. is carried out in which the reaction product I. is reacted with diols and/or polyols to form urethane functions. In general, step I and II. are carried out without solvent or by using non-protic solvents, wherein the reaction can be carried out batchwise or continuously. The reactions of step I. and II. are carried out in suitable equipment, e.g. stirred tanks, extruders, static mixers, kneading chambers. The reactions of step I. and II. can be carried out at room temperature, i.e. at temperatures in the range from 15 to 40° C., especially in the range from 15 to 25° C. Preferably, however, higher temperatures are used, in the 80 to 220° C. range, especially in the range from 80 to 120° C. The reactions of step I. and II. are carried out with exclusion of water. The reactions of step I. and step II. are preferably carried out solvent-free.

To accelerate the reactions of step I. and II., it is advantageously possible to use catalysts K) known in urethane chemistry, for example organometallic compounds such as compounds containing tin or zinc, salts, for example Zn(II) chloride, and/or bases. Suitable examples are carboxylates of Sn, Bi, Zn and other metals, for example dibutyltin dilaurate, tin octoate, zinc(II) ethylhexanoate, bismuth neodecanoate, tert-amines, for example 1,4-diazabicyclo[2.2.2]octane (DABCO), 1,8-diazabicyclo[5.4.0]undec-7-ene (DBU), 1,5-diazabicyclo[4.3.0]non-5-ene (DBN), triethylamine, amidine, guanidine, and quaternary ammonium salts, preferably tetraalkylammonium salts, and/or quaternary phosphonium salts.

Useful catalysts K) also include metal acetylacetonates. Examples thereof are zinc acetylacetonate, lithium acetylacetonate, iron acetylacetonate and tin acetylacetonate, alone or in mixtures. Useful catalysts are also quaternary ammonium acetylacetonates or quaternary phosphonium acetylacetonates.

For the reaction of step I. preference is given to using zinc acetylacetonate or zinc ethylhexanoate.

The catalysts used in step I. and II. may be identical or different.

The invention also relates to coating compositions, adhesives or sealants comprising or consisting of:
at least one, preferably one, alkoxysilane-functionalized and allophanate-functionalized urethane comprising the reaction product of
I.
A) at least one, preferably one, alkoxysilane group-containing monourethane A) of the formula 1

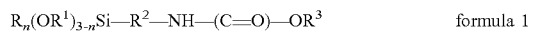

where $R_n$, $R^1$, $R^2$ and $R^3$ are each independently hydrocarbyl radicals having 1-8 carbon atoms, which may be linear, branched or cyclic, or else may be integrated together to form a cyclic system, and n is 0-2, and
B) at least one diisocyanate B),
in a molar ratio of A) to B) of from 1.0:1.5 to 1.0:0.6, preferably 1.15:1 to 0.85:1,
particularly preferably 1:1,
optionally in the presence of at least one catalyst K),
II.
and the subsequent reaction
C) with at least one diol and/or polyol C),
optionally in the presence of at least one catalyst K),
in the ratio of the NCO groups of reaction product I. to the OH groups of the diol and/or polyol II. C) of from 1.0:1.5 to 1.0:0.6, preferably 1.15:1 to 0.85:1, particularly preferably 1:1.

The invention also relates to the use of the alkoxysilane-functionalized and allophanate-functionalized urethanes according to the invention in coating compositions and paint compositions for metal, glass, plastic, wood, MDF (Middle Density Fibreboards) or leather substrates or other heat-resistant substrates.

The invention also relates to the use of the alkoxysilane-functionalized and allophanate-functionalized urethanes according to the invention in adhesive compositions for bonding of metal, plastic, glass, wood, MDF or leather substrates or other heat-resistant substrates.

The present invention is illustrated further by the following non-limiting examples from which further features, embodiments, aspects and advantages of the present invention may be discerned.

EXAMPLES

Ingredients:
Vestanat® EP-UPMS: Trimethoxysilylpropyl methyl carbamate (Evonik Resource Efficiency GmbH)
Vestanat® IPDI: isophorone diisocyanate (Evonik Resource Efficiency GmbH)
Vestanat® EP Cat 11 B: tetraethylammonium benzoate in butanol (Evonik Resource Efficiency GmbH)

Tegoglide® 410: Glide and antiblocking additive based on a polyether siloxane copolymer (Evonik Resource Efficiency GmbH)

1. Preparation

Alkoxysilane-functionalized and allophanate-functionalized urethane 1

I.

36.9 g of Vestanat® EP-UPMS, 0.04 g of zinc(II) ethylhexanoate and 34.7 g of Vestanat® IPDI were charged to a three-necked flask with reflux condenser, blanketed with nitrogen and heated with stirring to 100° C. After heating for 12 hours, an NCO content of 9.33% was obtained.

II.

The resulting allophanate was cooled and 8.37 g of pentanediol and 0.01% dibutyltin dilaurate (DBTL) were added and stirred at 60-65° C. for 17 h until an NCO content of <0.1% was achieved, and after ca. 3 h 20 g of butyl acetate were added in order to lower the viscosity. The alkoxysilane-functionalized and allophanate-functionalized urethane 1 thus obtained is a clear liquid with a viscosity of 3457 mPas (at 23° C.).

Alkoxysilane-functionalized and allophanate-functionalized urethane 2

I.

31.7 g of Vestanat® EP-UPMS, 0.04 g of zinc(II) ethylhexanoate and 29.8 g of Vestanat® IPDI were charged to a three-necked flask with reflux condenser, blanketed with nitrogen and heated with stirring to 100° C. After heating for 6 hours, an NCO content of 9.12% was obtained.

II.

The resulting allophanate was cooled and 13.5 g of dodecanediol and 0.01% dibutyltin dilaurate (DBTL) were added and stirred at 60-65° C. for several hours until an NCO content of <0.1% was achieved, then while still hot 20 g of 1-methoxypropyl-2-acetate were added in order to lower the viscosity. The alkoxysilane-functionalized and allophanate-functionalized urethane 2 thus obtained is a clear liquid with a viscosity of 1902 mPas (at 23° C.).

2. Preparation of Clearcoat Materials from the Alkoxysilane-Functionalized and Allophanate-Functionalized Urethanes as Coating Compositions For the formulation of the clearcoats according to the invention and the comparative examples, the components of the compositions shown in Table 1 and 2 were mixed together directly before processing.

The viscosity of the formulations, determined as the flow time in the DIN 4 cup at 23° C., was approximately 60 seconds.

TABLE 1

Composition of the inventive clearcoats of RT-curing systems
Data in % by weight

| Item | | I | II |
|---|---|---|---|
| 1 | Alkoxysilane-functionalized and allophanate-functionalized urethane 1 | 91.24 | |
| 2 | Alkoxysilane-functionalized and allophanate-functionalized urethane 2 | | 99.0 |
| 3 | 1,8-Diazabicyclo[5.4.0]undec-7-ene (DBU) | 0.92 | 1.0 |
| 4 | Tegoglide ® 410: | 0.05 | |
| 5 | Xylene | 7.79 | |

Based on solid, 1.25% by weight DBU was used respectively.

TABLE 2

Composition of the inventive clearcoats of hot-curing systems
Data in % by weight

| Item | | III | IV |
|---|---|---|---|
| 1 | Alkoxysilane-functionalized and allophanate-functionalized urethane 1 | 98.0 | |
| 2 | Alkoxysilane-functionalized and allophanate-functionalized urethane 2 | | 80.5 |
| 3 | Vestanat ® EP-CAT 11 B component d) | 2.0 | 1.6 |
| 4 | 1-Methoxypropyl-2-acetate | | 17.9 |

Based on solid, 1.25% by weight tetraethylammonium benzoate was used respectively.

Curing of the Clearcoats

To determine the mechanical characteristics, all coating materials were applied to phosphatized steel panels (Chemetall Gardobond 26S/60/OC) with a 100 μm doctor blade and cured at different baking conditions (RT is room temperature 23° C. Table 3; 22 minutes at 140° C., Table 4).

TABLE 3

Coating properties of the compositions I-II after curing at RT

| Composition | I | II |
|---|---|---|
| Pendulum hardness (König) [s] after 7 d | 188 | 154 |
| Erichsen cupping [mm] (EN ISO 1520) | 4 | 6 |
| MEK test [ASTM D 4752] (Double rubs, 1 kg applied weight) | 150. | >150 |

The coating properties of coatings I and II, which comprise the inventive alkoxysilane-functionalized and allophanate-functionalized urethanes 1 or 2, show high pendulum hardnesses and at the same time high flexibility (Erichsen cupping) at high MEK resistance.

TABLE 4

Coating properties of the compositions III-IV after curing at 140° C. (22 min)

| Composition | III | IV |
|---|---|---|
| Pendulum hardness (König) [s] after 1 d | 203 | 177 |
| Erichsen cupping [mm] (EN ISO 1520) | 0.5 | 1.0 |
| MEK test [ASTM D 4752] (Double rubs, 1 kg applied weight) | >150 | >150 |

The coating properties of coatings III and IV, which comprise the inventive alkoxysilane-functionalized and allophanate-functionalized urethanes 1 or 2, show high pendulum hardnesses and good chemical resistance.

The invention claimed is:

1. An alkoxysilane-functionalized and allophanate-functionalized urethane comprising the reaction product of
at least one alkoxysilane group-containing monourethane A) of formula 1

$$R_n(OR^1)_{3-n}Si-R^2-NH-(C=O)-OR^3 \quad \text{formula 1}$$

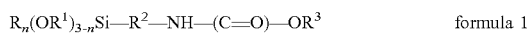

where $R_n$, $R^1$, and $R^3$ are each independently hydrocarbyl radicals having 1-8 carbon atoms, which may be linear, branched or cyclic, or else may be integrated together to form a cyclic system, and n is 0-2,
$R^2$ is a diradical having 1-8 carbon atoms, which may be linear, branched or cyclic, or else may be integrated together to form a cyclic system,
and
at least one diisocyanate B),
in a molar ratio of A) to B) of from 1.0:1.5 to 1.0:0.6,
optionally in the presence of at least one catalyst K),
and the subsequent the at least one reaction product
with at least one diol and/or polyol C),
optionally in the presence of at least one catalyst K),
in the ratio of the NCO groups of the at least one reaction product to the OH groups of the diol and/or polyol C of from 1.0:1.5 to 1.0:0.6.

2. An alkoxysilane-functionalized and allophanate-functionalized urethane, obtained by reacting
at least one alkoxysilane group-containing monourethane A) of the formula 1

$$R_n(OR^1)_{3-n}Si-R^2-NH-(C=O)-OR^3 \quad \text{formula 1}$$

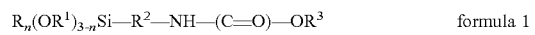

where $R_n$, $R^1$, and $R^3$ are each independently hydrocarbyl radicals having 1-8 carbon atoms, which may be linear, branched or cyclic, or else may be integrated together to form a cyclic system, and n is 0-2,
$R^2$ is a diradical having 1-8 carbon atoms, which may be linear, branched or cyclic, or else may be integrated together to form a cyclic system,
and
at least one diisocyanate B),
in a molar ratio of A) to B) of from 1.0:1.5 to 1.0:0.6,
in the presence of at least one catalyst K),
and subsequent reaction
with at least one diol and/or polyol C),
in the presence of at least one catalyst K),
in the ratio of the NCO groups of reaction product I. to the OH groups of the diol and/or polyol II. C) of 1.0:1.5 to 1.0:0.6.

3. The alkoxysilane-functionalized and allophanate-functionalized urethane according to claim 1, wherein $R_n$, $R^1$, and $R^3$ are at the same time or each independently methyl, ethyl, n-propyl, isopropyl, n-butyl, sec-butyl or tert-butyl.

4. The alkoxysilane-functionalized and allophanate-functionalized urethane according to claim 1, wherein n is equal to 0, $R^1$ and $R^3$ are at the same time or each independently methyl or ethyl, and $R^2$ is at the same time or each independently methylene or propylene.

5. The alkoxysilane-functionalized and allophanate-functionalized urethane according to claim 1, wherein n is equal to 0 and $R^2$ is methylene or propylene, and $R^1$ is methyl or ethyl and $R^3$ is $R^1$.

6. The alkoxysilane-functionalized and allophanate-functionalized urethane according to claim 1, wherein n is equal to 0, $R^1$ and $R^3$ are methyl and $R^2$ is propylene.

7. The alkoxysilane-functionalized and allophanate-functionalized urethane according to claim 1, wherein the diisocyanate B) is selected from isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-dicyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), or xylylene diisocyanate (MXDI), individually or in mixtures.

8. The alkoxysilane-functionalized and allophanate-functionalized urethane according to claim 1, wherein the diol and/or polyol C) is selected from ethylene glycol, propane-1,2-diol, propane-1,3-diol, diethylene glycol, dipropylene glycol, triethylene glycol, tetraethylene glycol, butane-1,2-diol, butane-1,4-diol, butylethylpropane-1,3-diol, methylpropane-1,3-diol, pentane-1,5-diol, bis(1,4-hydroxymethyl)cyclohexane (cyclohexanedimethanol), glycerol, hexanediol, neopentyl glycol, trimethylolethane, trimethylolpropane, pentaerythritol, bisphenol A, bisphenol B, bisphenol C, bisphenol F, norbornylene glycol, 1,4-benzyldimethanol, 1,4-benzyldiethanol, 2,4-dimethyl-2-ethylhexane-1,3-diol, 1,4-butylene glycol, 2,3-butylene glycol, di-β-hydroxyethylbutanediol, hexane-1,6-diol, octane-1,8-diol, decanediol, dodecanediol, cyclohexanediol, 3(4),8(9)-bis(hydroxymethyl)tricyclo[5.2.1.0$^{2,6}$]decane (dicidol), 2,2-bis(4-hydroxycyclohexyl)propane, 2,2-bis[4-(β-hydroxyethoxy)phenyl]propane, 2-methylpropane-1,3-diol, 2-methylpentane-1,5-diol, 2,2,4(2,4,4)-trimethylhexane-1,6-diol, hexane-1,2,6-triol, butane-1,2,4-triol, tris(β-hydroxyethyl) isocyanurate, mannitol, sorbitol, polypropylene glycols, polybutylene glycols, xylylene glycol or neopentyl glycol hydroxypivalate, alone or in mixtures.

9. The alkoxysilane-functionalized and allophanate-functionalized urethane according to claim 1, wherein the diol and/or polyol C) is selected from ethylene glycol, triethylene glycol, butane-1,4-diol, propane-1,2-diol, pentane-1,5-diol, hexane-1,6-diol, cyclohexanedimethanol, decanediol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, trimethylolpropane, 2,2-dimethylpropane-1,3-diol (neopentyl glycol), neopentyl glycol hydroxypivalate or cis/trans-cyclohexane-1,4-diol, alone or in mixtures.

10. The alkoxysilane-functionalized and allophanate-functionalized urethane according to claim 1, wherein the diol and/or polyol C) is selected from pentane-1,5-diol, hexane-1,6-diol, dodecane-1,12-diol, 2,2,4-trimethylhexane-1,6-diol, 2,4,4-trimethylhexane-1,6-diol, 2,2-dimethylbutane-1,3-diol, 2-methylpentane-2,4-diol, 3-methylpentane-2,4-diol, 2,2,4-trimethylpentane-1,3-diol, 2-ethylhexane-1,3-diol, 2,2-dimethylhexane-1,3-diol, 3-methylpentane-1,5-diol, 2-methylpentane-1,5-diol, 2,2-dimethylpropane-1,3-diol (neopentyl glycol) or cis/trans-cyclohexane-1,4-diol, alone or in mixtures.

11. The alkoxysilane-functionalized and allophanate-functionalized urethane according to claim 1, wherein the diol and/or polyol C) is selected from hydroxyl group-containing polyesters, polyethers, polyacrylates, polycarbonates or polyurethanes having an OH number of 20 to 500 mg KOH/g and a mean molar mass of 250 to 6000 g/mol, alone or in mixtures.

12. The alkoxysilane-functionalized and allophanate-functionalized urethane according to claim 1, wherein the diol and/or polyol C) is selected from hydroxyl group-containing polyesters or polyacrylates having an OH number of 50 to 250 mg KOH/g and a mean molecular weight of 500 to 6000 g/mol, alone or in mixtures.

13. The alkoxysilane-functionalized and allophanate-functionalized urethane according to claim 1, wherein the catalyst K) is selected from the group consisting of metal carboxylates, tert-amines, amidine, guanidine, quaternary ammonium salts, tetraalkylammonium salts, quaternary phosphonium salts, metal acetylacetonates, quaternary ammonium acetylacetonates, quaternary phosphonium acetylacetonates, carboxylic acids, aluminium alkoxides, zirconium alkoxides, titanium alkoxides and/or boron alkoxides and/or esters thereof, phosphorus- and nitrogen-containing catalysts, and sulphonic acids, alone or in mixtures.

14. The alkoxysilane-functionalized and allophanate-functionalized urethane according to claim 1, wherein the catalyst K) is zinc acetylacetonate and/or zinc ethylhexanoate.

15. The method for preparing alkoxysilane-functionalized and allophanate-functionalized urethanes according to claim 1, by reacting
at least one alkoxysilane group-containing monourethane A) of formula 1

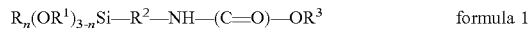    formula 1 wherein $R_n$, $R^1$, and $R^3$ independently of one another represent hydrocarbon radicals having 1-8 carbon atoms, wherein these may be linear, branched or cyclic or else may be integrated together to form a cyclic system, and n represents 0-2,
$R^2$ is a diradical having 1-8 carbon atoms, which may be linear, branched or cyclic, or else may be integrated together to form a cyclic system,
and
at least one diisocyanate B) having NCO groups,
in a molar ratio of A) to B) of from 1.0:1.5 to 1.0:0.6, optionally in the presence of at least one catalyst K),
and the subsequent the at least one reaction product
with at least one diol and/or polyol C),
optionally in the presence of at least one catalyst K),
in the ratio of the NCO groups of the at least one reaction product to the OH groups of the diol and/or polyol C of 1.0:1.5 to 1.0:0.6.

16. The method according to claim 15, wherein the reaction of step I. or II. is carried out at temperatures in the range from 15 to 40° C.

17. The method according to claim 15, wherein the reaction of step I. or II. is carried out at temperatures in the range from 80 to 220° C.

18. The method according to claim 15, wherein the reaction of step I. is carried out in the presence of zinc acetylacetonate and/or zinc ethylhexanoate as catalyst K).

19. The method according to claim 15, wherein the reaction of the NCO groups of B) with the OH groups of the diol and/or polyol C is carried out at temperatures in the range of 30-150° C.

20. The method according to claim 15, wherein the NCO groups of the at least one reaction product are reacted with the OH groups of the diol and/or polyol C in the ratio of NCO groups to OH groups of from 0.8:1 to 1.2:1.

21. A coating composition, adhesive or sealant comprising:
at least one alkoxysilane-functionalized and allophanate-functionalized urethane comprising the reaction product of
at least one alkoxysilane group-containing monourethane A) of formula 1

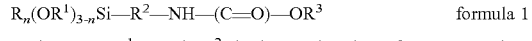    formula 1 wherein $R_n$, $R^1$, and $R^3$ independently of one another represent hydrocarbon radicals having 1-8 carbon atoms, wherein these may be linear, branched or cyclic or else may be integrated together to form a cyclic system, and n represents 0-2, $R^2$ is a diradical having 1-8 carbon atoms, which may be linear, branched or cyclic, or else may be integrated together to form a cyclic system, and at least one diisocyanate B), in a molar ratio of A) to B) of from 1.0:1.5 to 1.0:0.6, in the presence of at least one catalyst K), and the subsequent the at least one reaction product with at least one diol and/or polyol C), in the presence of at least one catalyst K), in the ratio of the NCO groups of the at least one reaction product to the OH groups of the diol and/or polyol C of 1.0:1.5 to 1.0:0.6.

* * * * *